United States Patent [19]

Lerner

[11] 3,965,891

[45] June 29, 1976

[54] IUD PREPACKAGED IN A TUBULAR INSERTER

[75] Inventor: Irwin S. Lerner, Greenwich, Conn.

[73] Assignee: A. H. Robins Company, Incorporated, Richmond, Va.

[22] Filed: Nov. 18, 1974

[21] Appl. No.: 524,816

Related U.S. Application Data

[60] Division of Ser. No. 447,262, March 1, 1974, Pat. No. 3,857,391, which is a continuation of Ser. No. 187,373, Oct. 7, 1971, abandoned.

[52] U.S. Cl. ............................................. 128/130
[51] Int. Cl.² ........................................... A61F 5/46
[58] Field of Search ........................... 128/127–130, 128/263, 264, 267

[56] References Cited
UNITED STATES PATENTS

| | | | |
|---|---|---|---|
| 3,515,132 | 6/1970 | McKnight | 128/130 |
| 3,516,403 | 6/1970 | Cournut | 128/130 |
| 3,777,748 | 12/1973 | Abramson | 128/130 |
| 3,783,861 | 1/1974 | Abramson | 128/127 |

Primary Examiner—Lawrence W. Trapp
Attorney, Agent, or Firm—Strauch, Nolan, Neale, Nies & Kurz

[57] ABSTRACT

A relatively narrow diameter tubular inserter adaptable for use with a wide variety of intrauterine devices, having lateral slots therein for retaining a resilient intrauterine device in an undeformed state during shipment and storage prior to insertion. The intrauterine device is moved to a deformed state within the relatively narrow tube just prior to insertion, and ejected therefrom into its normal expanded state within the uterine cavity, whereupon the tube is withdrawn.

13 Claims, 23 Drawing Figures

U.S. Patent June 29, 1976 3,965,891
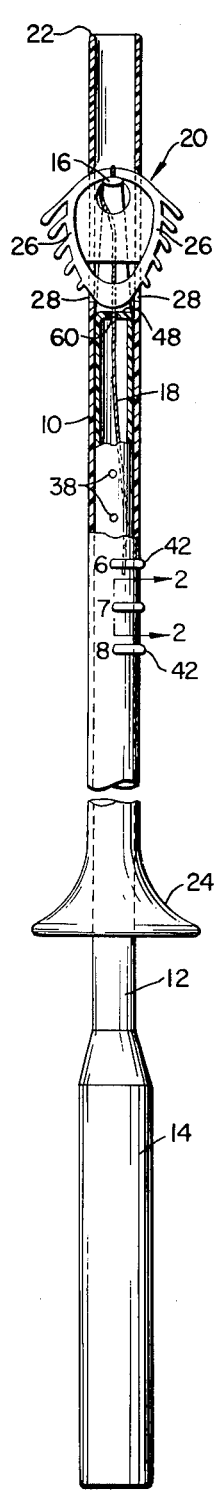
FIG. 1
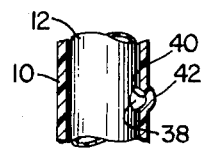
FIG. 2
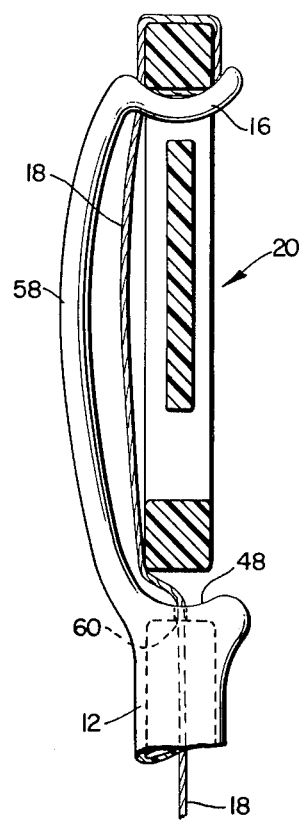
FIG. 3
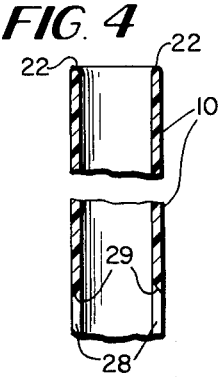
FIG. 4
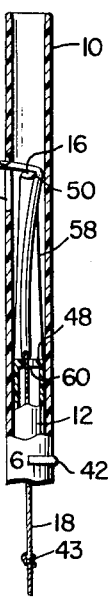
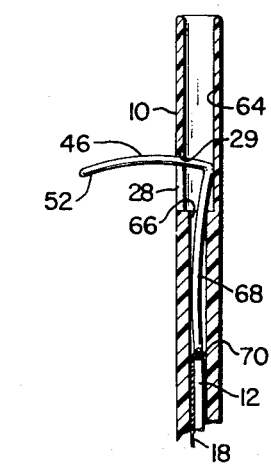
FIG. 21
FIG. 22
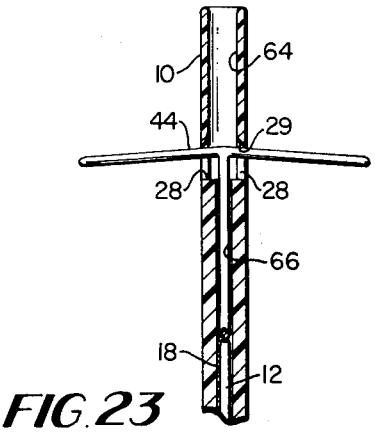
FIG. 23

FIG. 9
FIG. 10
FIG. 11
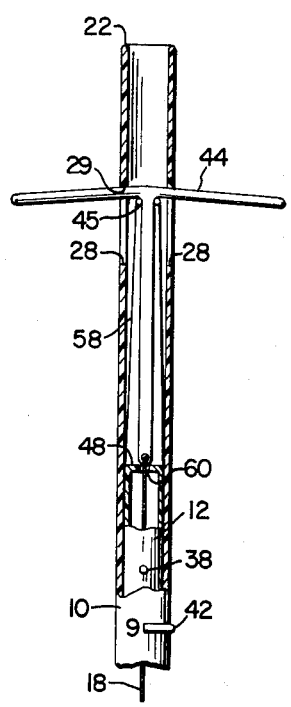
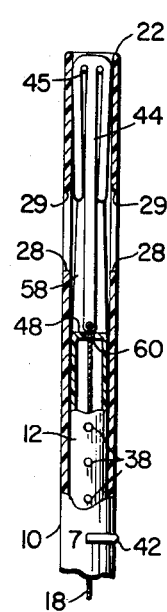
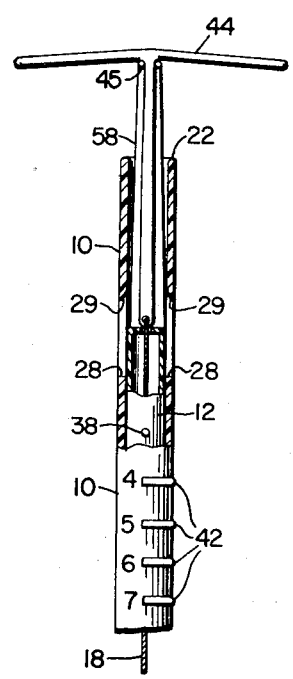
FIG. 12
FIG. 13
FIG. 14
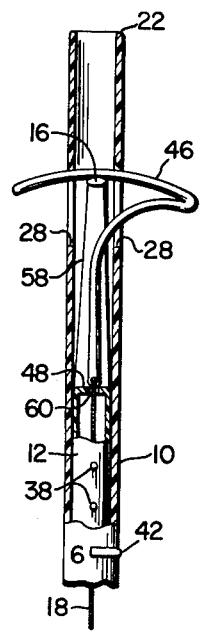
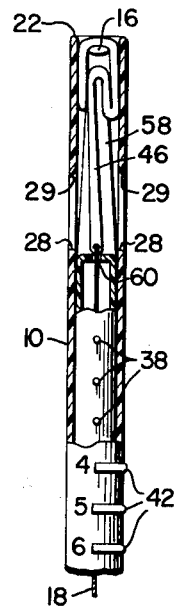
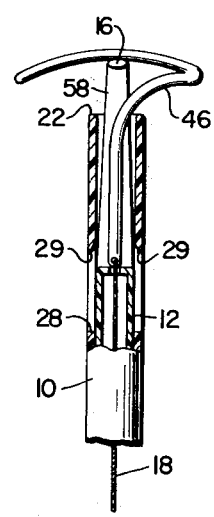

IUD PREPACKAGED IN A TUBULAR INSERTER

CROSS-REFERENCE TO RELATED APPLICATIONS

This application is a division of application Ser. No. 447,262 filed Mar. 1, 1974, now U.S. Pat. No. 3,857,391, which is in turn a continuation of application, Ser. No. 187,373, filed Oct. 7, 1971, now abandoned.

The present invention is useful as an inserter for intrauterine devices of the type shown, described and claimed in prior co-pending application Ser. No. 775,729, filed Nov. 14, 1968, now U.S. Pat. No. 3,633,574, dated Jan. 11, 1972, and assigned to the same assignee as the instant invention.

The inserter described and claimed herein differs substantially from the intrauterine device inserter shown, described and claimed in my prior U.S. Pat. No. 3,771,520, dated Nov. 13, 1973.

BACKGROUND OF THE INVENTION

1. Field of the Invention

The invention relates to the field of intrauterine contraceptive devices, now popularly known as "IUD's" and specifically to a tubular inserter useful for insertion of any one of a wide variety of IUD's.

2. Discussion of the Prior Art

Background information concerning female contraceptive agents in general and the distinct advantages of the intrauterine device or IUD over other contraceptive agents is set forth in detail in U.S. Pat. Nos. 3,633,574 and 3,771,520, identified above.

One of the few remaining factors retarding even more widespread acceptance and use of the IUD as a contraceptive agent is the experience of IUD insertion. The development of satisfactory IUD insertion means, readily adaptable to a wide variety of currently popular IUD's will be an important contribution to the art. Such insertion means must firmly engage the IUD during insertion through the cervical canal and positioning in the fundal region of the uterine cavity, yet be easily disengaged therefrom for withdrawal of the inserter. An inserter should be manipulable by one hand only since the other hand of the person performing the insertion will be employed in moving the uterus from its normal anteflexed position to a state of traction whereby the IUD may be easily inserted; this is accomplished by grasping the cervical anterior lip with a tenaculum and exerting a pulling force.

Preferably, IUD's are dispensed as a prepackaged, sterilized assembly with the IUD in place on the inserter so that upon breaking the sterile seal, the device is immediately ready for insertion. A most popular form of inserter is a relatively narrow diameter tube having a rounded, blunt end which will pass through the cervical canal easily and will not damage or injure the fundus upon contact therewith. Such tubes as currently marketed contain a resilient IUD which is deformed into a narrow elongate shape within the tube so that the assembly is ready for immediate use. Once expulsed from the insertion tube within the uterine cavity, the IUD is supposed to resume its normal, undeformed expanded shape.

Unfortunately, the period of time from packaging to use may be quite extended, and the IUD may lose its resilient nature thereby becoming permanently deformed and unable to spring back into its planned expanded configuration once positioned within the uterine cavity. To date, the only answer to the problem has been to package the IUD and its tubular inserter in unattached fashion. This solution yields two unsatisfactory results. First, unnecessary handling is required to assemble the unit prior to insertion, such handling being inherently time-consuming and potentially destructive of the sterile environment of the IUD and its inserter. Secondly, the handler may put the unit together incorrectly thereby either irretrievably jamming the IUD within its tubular inserter, or injuring the cervical canal and uterine cavity in attempting to insert an improperly mounted IUD.

U.S. Pat. No. 3,515,132 issued to Charles A. McKnight recognizes the problem of shelf life deterioration of an IUD packaged in a deformed condition, but provides no solution other than to package the IUD separately from the tubular inserter. The tubular inserter disclosed in the patent includes a lateral port adjacent an internal plunger for frictionally engaging an IUD withdrawal cord during insertion, but the tubular inserter is specifically not designed to enter the uterine cavity, nor does the lateral tube port cooperate in any manner in housing the IUD in a normal, expanded configuration.

In contradistinction, the present invention provides a tubular inserter which is packaged with the IUD housed therein in its normal expanded condition. Immediately prior to insertion, the IUD is easily deformed into a compressed shape within the tube and readily expulsed therefrom into its normal, expanded configuration within the uterine cavity. Thus, prolonged deformation of the IUD is avoided, which considerably lengthens the shelf life of such items.

The inserter of the present invention is adaptable for use with a wide variety of IUD's. For example, it may be used with the type of IUD disclosed in the aforenoted U.S. Pat. No. 3,633,574; with open end IUD's, two of which are known in the art as the T and the 7; with closed loop IUD's such as the Birnberg bow; and with IUD's having a plurality of extended winglike projections for engaging side walls of the uterine cavity to aid in preventing expulsion of the IUD therefrom. The T-form of IUD is disclosed in U.S. Pat. No. 3,533,406, issued to Howard J. Tatum, and the Birnberg bow is fully disclosed in U.S. Pat. No. 3,230,953, issued to Charles H. Birnberg.

SUMMARY OF THE INVENTION

It is a principal object of the invention to provide the combination of a relatively narrow diameter inserter for high fundal positioning of an IUD which may be prepackaged with the IUD in normal, expanded configuration, house the IUD in a deformed elongate condition during insertion, and release the IUD in an expanded state within the uterine cavity and an IUD.

It is another object of the invention to provide the combination of an IUD and a universal tubular IUD inserter having one or more windows for housing the IUD in its normal expanded state with portions projecting through the windows prior to insertion.

It is another object of the invention to provide the combination of an IUD and a universal tubular IUD inserter having plunger means for moving the IUD to an elongated deformed position within the tube to ease insertion of the device into the cervical canal, and for expulsion of the IUD from the tube, within the uterine cavity.

It is another object of the invention to provide the combination of an IUD and a universal tubular IUD inserter which may be prepackaged with the IUD therein in a normal, expanded configuration thereby considerably prolonging the shelf life of the IUD.

A further object of the invention is to provide a universal tubular inserter prepackaged with an expanded IUD therein wherein minimal handling is required to move the IUD into a deformed condition in the tube prior to insertion and positioning.

Another object of the invention is to provide a universal tubular inserter prepackaged with an expanded IUD therein which requires minimal handling for insertion of the IUD and is disposable after use, thus promoting an optimum sanitary environment for IUD insertion.

Another object of the invention is to provide a universal tubular IUD inserter having cooperating members formed of flexible material which will conform itself to the natural contours of the uterus during insertion and positioning.

Further novel features and other objects of this invention will become apparent from the following detailed description, discussion and the appended claims taken in conjunction with the accompanying drawings.

BRIEF DESCRIPTION OF DRAWINGS

Preferred structural embodiments of intrauterine devices and inserter combination invention are disclosed in the accompanying drawings in which:

FIG. 1 is an elevational view, partially in section, illustrating a preferred form of the invention;

FIG. 2 is a sectional view taken along lines 2—2 of FIG. 1 and drawn to an enlarged scale;

FIG. 3 is an enlarged, partial sectional view showing mounting of the IUD upon the interior plunger portion of the inserter;

FIG. 4 is an enlarged, fragmentary, sectional view of the insertion end of the tubular inserter;

FIGS. 9, 10 and 11 are partial sectional side views showing prepackaged; deformed; and expulsed attitudes of a T-IUD with the tubular inserter;

FIGS. 12, 13 and 14 are views similar to FIGS. 9, 10 and 11 showing the tubular inserter used with a 7-IUD;

FIG. 21 is a view similar to FIG. 13 illustrating an alternative embodiment of insertion tube used with a 7-IUD;

FIG. 22 is a view similar to FIG. 21 illustrating yet another embodiment of insertion tube and an alternative plunger used with a 7-IUD; and FIG. 23 is a view similar to FIG. 22 showing a tube and plunger similar to those of FIG. 21 used with a T-IUD.

DESCRIPTION OF THE PREFERRED EMBODIMENTS

Figure 5:
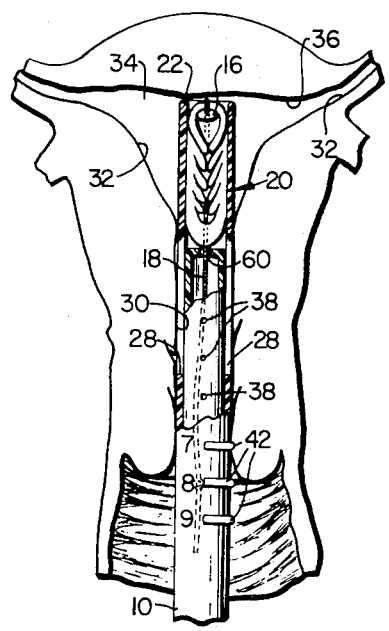
FIGS. 5 through 8 are sequential views illustrating positioning of an IUD still within the insertion tube in the uterine cavity; retraction of the tube from the IUD and expansion of the IUD within the uterine cavity; withdrawal of the tubular inserter from the cervical canal; and final disposition of an IUD within the uterine cavity including insertion depth confirmation.

A tubular inserter 10 includes an IUD expelling plunger 12 coaxially mounted therein which may include a handle portion 14 at the lower, terminal end thereof. The upper end of plunger 12 is fashioned into an IUD saddle shaped retention seat 16 and, in a preferred embodiment, is hollow throughout its length to accommodate a withdrawal string 18 of an IUD 20. The front, cervix entry end 22 of tubular inserter 10 is annularly rounded to ease insertion of the device into a cervical canal and uterine cavity (FIG. 4). The rear terminal end of tubular inserter 10 may be fashioned into a flange 24 for grasping by the hand of an operator during insertion and positioning of IUD 20.

As illustrated in FIG. 1, a resilient IUD 20 is housed within tubular inserter 10 in its normal, undeformed expanded configuration with lateral winglike members 26 projecting through a pair of laterally offset windows 28 formed one on either side adjacent the front, entry end 22 of tubular inserter 10. With this unique arrangement of parts, the entire unit can be prepackaged in a sterile environment with the IUD properly positioned in the tube 10 to be inserted into a cervical canal and uterine cavity, yet during the time between packaging and readying for use, IUD 20 remains undeformed, thus significantly prolonging the shelf-life of the device.

Immediately prior to insertion, all that need be done is to grasp handle 14 and tube flange 24 in order to move IUD 20 slightly upwardly within tube 10 so that IUD 20 assumes an elongate, deformed configuration as illustrated in FIG. 5. As an assist in this operation, the upper edge of each window 18 is rounded upwardly inwardly (FIG. 4) at 29 so that IUD 20 passes easily into tubular inserter 10. In this mode, IUD 20 is entirely housed within tube 10, the tube being of relatively narrow diameter so as to pass through a cervical canal 30 easily. It should be noted that such insertion preparation consumes a minimal amount of time and avoids any handling of IUD 20 and the adjacent portions of tube 10 so as to maintain the sterile integrity of the entire device.

Figure 6:
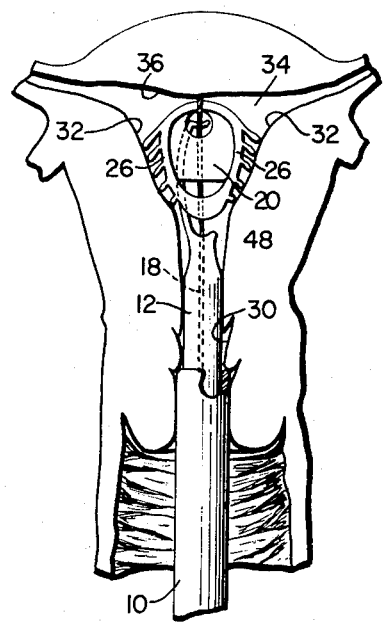

FIG. 6 depicts expulsion of IUD 20 from tubular inserter 10 whereupon IUD 20 will immediately resume its normal, undeformed expanded configuration, with winglike projections 26 in extended position enabling engagement with the side walls 32 of uterine cavity 34 to aid in preventing expulsion of IUD 20 from the uterus.

Figure 7:
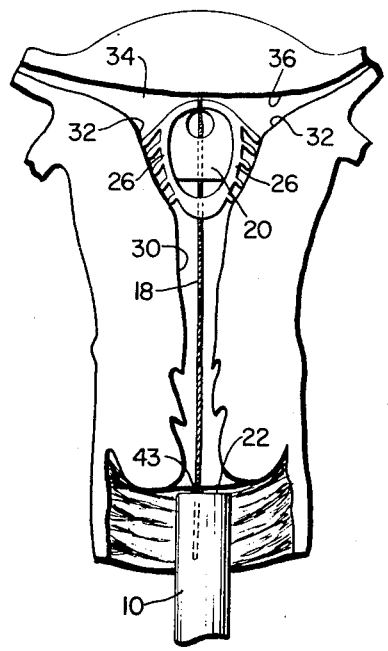
Figure 8:
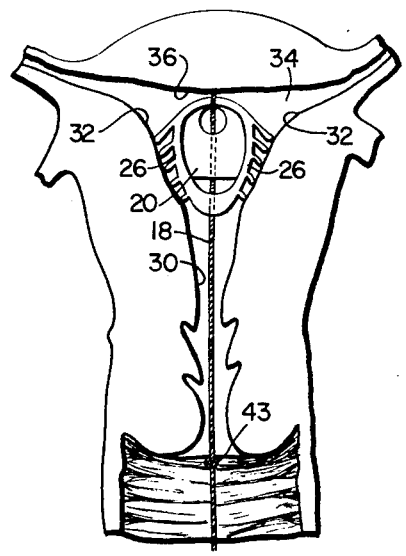

The insertion and location methodology just described is necessarily performed without benefit of visual assurance that IUD 20 is properly positioned within uterine cavity 34. Other means must be provided not only to assure proper positioning of IUD 20, but also to minimize the possibility of injury to fundus 36 of uterine cavity 34. To this end, tactile disposition means indicating relative displacement between plunger 12 and tubular inserter 10 is provided so that the operator knows at all times during the insertion process the precise disposition and placement of IUD 20 within uterine cavity 34. In a preferred embodiment (FIGS. 1 and 2) such means include equispaced axially aligned semispherical portions 38 formed as projections along the outer surface of plunger 12, cooperating with a mating set of equispaced, axially aligned detents or recesses 40 formed along the inner surface of tubular inserter 10. Preferably, adjacent pairs of projections 38 and recesses 40 are spaced about 1 cm. apart. As tube 10 is slid downwardly over plunger 12 to expel IUD 20 (FIGS. 5 and 6) a tactile click will be transmitted to the hand of the operator, signalling him that in fact IUD 20 is being properly expelled. Simultaneously, the operator can determine that IUD 20 is placed in the proper plane within the uterus (FIGS. 5-8) in that should any relative rotation occur between tube 10 and plunger 12 during insertion, the tactile click provided by normally axially aligned members 38, 40 will not be felt. In this embodiment, IUD 20 is approximately 21 mm. in length, so that upon sensing two clicks as tube 10 is slid downwardly over plunger 12, the operator will know that IUD 20 has in fact been expelled from tube 10, and that then both tubular inserter 10 with plunger 12 may be withdrawn from the uterus altogether, as illustrated in FIGS. 7 and 8.

The usual practice in the prior art of tubular inserters has been to insert the tube to the internal os and then to hold the tube stationary while expelling the IUD therefrom by continued forward motion of the plunger, as disclosed in U.S. Pat. No. 3,515,132, by way of example. There are at least two distinct disadvantages in this methodology. First, it is extremely difficult to determine the precise location of the internal os, by any reasonable sounding process. Secondly, if the tubular inserter is not properly located, the delicate uterine cavity fundus may be injured or even ruptured by expulsion step, if the tube is inserted too far, or the IUD may be deposited partially or entirely within the cervical canal where it has little chance of accomplishing its intended function. On the other hand, tubular inserter 10 with IUD 20 of the present invention is intended to be inserted all the way to fundus 36 as shown in FIG. 5. Injury to fundus 36 will not occur, due to the annular rounding of tube end 22. Proper depth location for the IUD 20 being placed into the uterus is assured by contact of tube end 22 with fundus 36. By then withdrawing tube 10 over plunger 12, instead of moving plunge 12 upwardly within tube 10 as in the prior art practice, possibility of injury to the uterine cavity is minimized, since movement of the parts is now in a direction away from fundus 36 instead of towards it.

A discussion of the entire IUD insertion process is now in order. First, the vagina of the user is dilated with a speculum followed by cleansing of the cervix (not shown). Then, the exterior of the cervix is grasped by a tenaculum to draw the uterus from its normal anteflexed position into a state of traction so that the axis of the uterus is generally aligned with the axis of the vagina, to ease insertion of the IUD into the cervical canal and uterine cavity (not shown). A sounder is next employed to measure depth and determine the particular axis and contour of the uterus. Then the IUD itself is inserted and positioned as previously described. Assurance of proper insertion depth may be provided by a series of gradations 42 affixed exteriorally of tubular inserter 10 which indicate the distance from tube end 22 to the point where an individual gradation 42 appears on tubular inserter 10. As is the usual gynecological practice, these measurements are demarcated in centimeters. A final confirmation of proper IUD insertion depth may be provided by a knot 43 located near the lower free end of IUD withdrawal string 18; knot 43 is usually positioned about 7 cm. from the upper end of IUD 20 (FIG. 8).

The present invention is easily adaptable to a wide variety of IUD's, as is illustrated by FIGS. 9 through 21.

FIGS. 9, 10 and 11 show a T-IUD 44 positioned with the major portion thereof within tubular inserter 10 prior to insertion preparation, deformed to an elongate configuration within tube 10 for insertion into the uterus, and expelled therefrom as by drawing tube 10 down over plunger 12 once IUD 44 is positioned in the uterine cavity. The outer end of seating head 16 of plunger 12 may be bifurcated at 45 to centrally accommodate T-IUD 44 at the intersection of its stem and cross member.

FIGS. 12, 13 and 14 are similar to FIGS. 9, 10 and 11 but illustrate the invention being used with a 7-IUD 46. Saddle 16 may be placed centrally beneath the cross member of 7-IUD 46 (FIG. 12). As plunger 12 is moved upwardly to compress 7-IUD 46 within tube 10 just prior to uterine insertion, lower curved terminal seat 48 of plunger 12 engages the base of the stem of IUD 46 so that the portions of IUD 46 projecting through windows 28 may fold inwardly of the tube 10 as they pass curved window edges 29. When tube 10 is drawn down over plunger 12 to expel IUD 46 within the uterine cavity, IUD 46 assumes its normal, undeformed configuration (FIG. 14).

FIG. 21 illustrates an alternative embodiment of the number and disposition of windows 28 to accommodate a 7-IUD 46 or equivalent structure. Tubular inserter 10 is provided with but one window 28, with saddle 16 arranged to engage IUD 46 adjacent fillet 50 thereof. Thus, only free end 52 of IUD 46 projects from tubular inserter 10 prior to withdrawal of the IUD into tube 10. As in the embodiment shown in FIGS. 12, 13 and 14, movement of plunger 12 upwardly in tube 10 will retract the projecting portion 52 of IUD 46 into tubular inserter 10.

FIG. 22 discloses an alternative embodiment of a tubular inserter and plunger used with a 7-IUD. Tubular inserter 10 has but one window 28 but comprises internal passage portions 64 and 66 having differing internal diameters but being coaxially aligned. Stem 68 of 7-IUD 46 is stored in the lower, smaller diameter passage portion 66. Plunger 12 is solid in this embodiment and has an IUD engaging end 70 which may be slightly concave to assure firm seating of IUD 46 thereon when the plunger is operated. Pushing on the plunger 12 will retract IUD 46 into the upper, larger diameter passage portion 64 of tubular inserter 10 where free end 52 and stem 68 will lie approximately parallel to one another, prior to expulsion of the IUD within the uterus. In a preferred embodiment, the internal diameter of upper portion 64 will be about twice the diameter of the stem of IUD 46 to comfortably accommodate end 52 and stem 68 therewithin. Lower portion 66 has a diameter of about 1.5 times the diameter of IUD 46, since only the stem is received therein. Plunger 12 will have a diameter somewhat smaller than this, so as to slide easily within the tubular inserter and also to provide sufficient space for withdrawal cord 18 to fit therealongside without binding between the inserter and plunger during IUD insertion.

The embodiment disclosed in FIG. 23 comprises a plunger and inserter tube used with a T-IUD, similar in structure and function to the plunger and inserter disclosed in FIG. 22 except that upper portion 64 is about 2.5 times the diameter of the T-IUD, or more so as to accommodate the stem and both halves of the head of T-IUD 44 with minimal distortion being imparted to tubular inserter 10. In the case of both of the embodiments illustrated in FIGS. 22 and 23, the diameter dimensions given are only approximations and the drawings are not necessarily to scale. However, the diameter sizes given yield a satisfactorily operable inserter and plunger.

Figure 15:
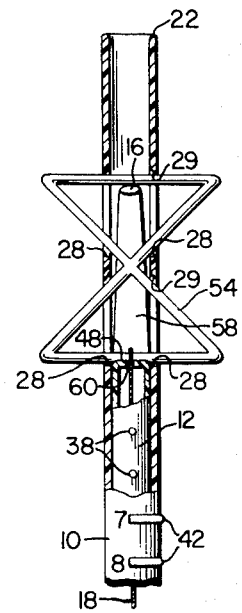
FIGS. 15, 16 and 17 are views similar to FIGS. 9, 10 and 11 illustrating the invention used with a Birnberg bow IUD.
Figure 16:
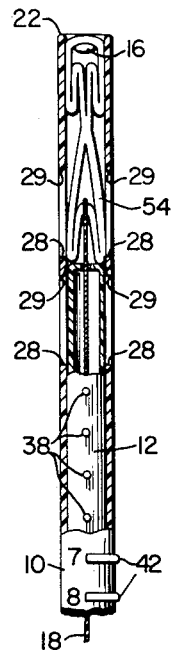
Figure 17:
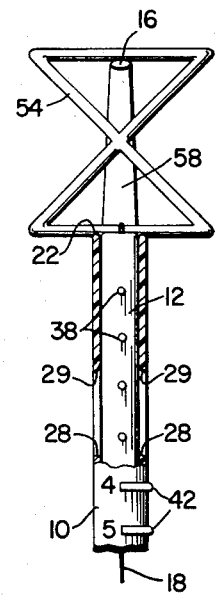

FIGS. 15, 16 and 17 are similar to FIGS. 9, 10 and 11 except that a Birnberg bow 54 is shown, and two sets of planarly aligned windows 28 are provided in tubular inserter 10 to house the major portion of IUD 54 prior to insertion preparation. As IUD 54 is expulsed into the uterine cavity by drawing tube 10 downwardly over plunger 12, the lower projecting portions of IUD 54 will "rachet" past upper windows 28 of tube 10 which provide a further tactile sigal to the operator that the IUD expulsion process is proceeding properly.

Figure 18:
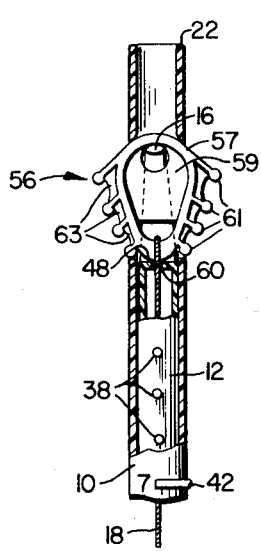
FIGS. 18, 19 and 20 are views similar to FIGS. 9, 10 and 11 showing the invention used with a multiple laterally winged or spur type of IUD.
Figure 19:
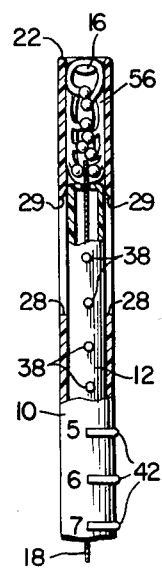
Figure 20:
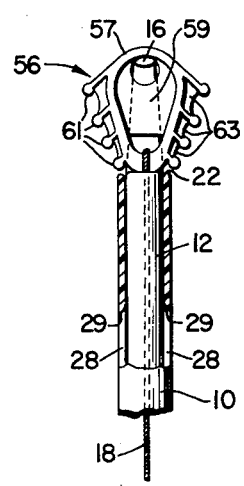

FIGS. 18, 19 and 20 are also similar to FIGS. 9, 10 and 11, illustrating the invention used with an IUD 56 comprising a perimeter 57, central membrane 59, and a plurality of projecting spurs 61 which may be webbed at 63 for better IUD retention once in place within the uterus.

The configuration of plunger 12 with its saddle 16 and lower curved terminal seat 48 is the same for use with inserting any IUD suitable for this invention. Referring to FIG. 3, seat 48 and saddle 16 are interconnected by a long slender curved neck 58. Members 16, 48 and 58 are all gently rounded to minimize the possibility of injury to the walls of the uterus and cervical canal during insertion. Plunger 12 is generally hollow throughout its length and includes an opening 60 formed in seat 48 to allow withdrawal string 18 to be housed within plunger 12 during the insertion process so as not to interfere with relative moving parts of the invention. Preferably, although not necessarily, saddle 16 and lower seat 48 are disposed apart a distance greater than the undeformed length of an IUD mounted thereon (FIG. 3) so during the time the IUD is deformed within tube 10, both saddle 16 and seat 48 engage upper and lower portions of the IUD respectively, but upon expulsion of the IUD from the tube 10 within the uterus, only saddle 16 need be disengaged, as by rotating the invention a quarter turn (FIG. 6), seat 48 and the IUD becoming disengaged by the return of the IUD being inserted to its normal, undeformed position within the uterus.

The invention may be embodied in other specific forms without departing from the scope, spirit or essential characteristics thereof. The present embodiments are, therefore, to be considered in all respects as illustrative and not restrictive, the scope and spirit of the invention being indicated by the appended claims rather than by the foregoing description, and all changes which come within the meaning and range of equivalency of the claims are, therefore, intended to be embraced therein.

What is claimed and desired to be secured by letters patent is:

1. The combination of a resilient intrauterine device comprising a major portion, and laterally extending portion means, and an inserter for high fundal positioning of said intrauterine device, said inserter comprising an elongate tubular body having a front, cervix entry and intrauterine device expulsion end and a rear terminal end, and means for housing said major portion of said resilient intrauterine device within said tubular body with said intrauterine device being in a substantially undeformed configuration; whereby said intrauterine device may be deformed into an elongate shape within said tubular body prior to insertion of said inserter into placement position relative to a uterus and thereafter expelled into its substantially undeformed configuration within a uterine cavity.

2. The intrauterine device and inserter combination of claim 1 wherein said means for housing said major portion of said intrauterine device within said tubular body comprise means defining at least one window through a side wall of said tubular body, said window being arranged to retain said intrauterine device laterally extending portion means projecting through said window in substantially undeformed configuration.

3. The intrauterine device and inserter combination of claim 1 wherein said means for housing said major portion of said intrauterine device within said tubular body comprise means defining a pair of windows disposed one on each side of said tubular body, said windows being arranged to retain said intrauterine device laterally extending portion means projecting through said windows in substantially undeformed configuration.

4. The intrauterine device and inserter combination of claim 1 wherein said means for housing said major portion of said intrauterine device within said tubular body comprise at least two pairs of windows through the sidewall of said tubular body, one of said window pairs displaced axially with respect to the other along the long axis of said tubular body, said windows being arranged to retain said intrauterine device laterally extending portion means projecting through said windows in substantially undeformed configuration.

5. The intrauterine device and inserter combination of claim 1 wherein said means for housing said major portion of said intrauterine device within said tubular body is located adjacent said tubular body front end.

6. The intrauterine device and inserter combination of claim 1 wherein said means for housing said major portion of said intrauterine device within said tubular body comprise means defining a pair of windows in said tubular body, the ends of said windows closest to said tubular body front end being located equidistant from said tubular body front end.

7. The intrauterine device and inserter combination of claim 6 wherein said pair of windows have equal width and equal length dimensions.

8. The intrauterine device and inserter combination of claim 7 wherein said pair of windows are aligned in the same plane containing the axis of the tubular inserter.

9. The intrauterine device and inserter combination of claim 1 wherein said means for housing said major portion of said intrauterine device within said tubular body consists of one window through a side wall of said tubular body, said one window being arranged to retain said portion means of said intrauterine device projecting through said one window.

10. The intrauterine device and inserter combination of claim 1, further comprising intermediate intrauterine device disposition means located between said intrauterine device major portion housing means and said tubular body front entry end for positioning said resilient intrauterine device substantially wholly within said inserter prior to said insertion of said inserter into placement position relative to a uterus.

11. The intrauterine device and inserter combination of claim 1, further comprising plunger means within said tubular body for moving said intrauterine device to a deformed shape within said tubular body and for expelling said intrauterine device from said tubular body.

12. The intrauterine device and inserter combination of claim 11 wherein said tubular body and said plunger means are made of flexible, substantially physiologically inert material.

13. The intrauterine device and inserter combination of claim 1 wherein said means for housing said major portion of said intrauterine device within said tubular body includes window means opening through the wall of said tubular body, said window means being arranged to retain said intrauterine device laterally extending portion means disposed through the wall of said tubular body in a substantially undeformed configuration.

* * * * *